United States Patent [19]

Uhrig et al.

[11] Patent Number: 5,420,315

[45] Date of Patent: May 30, 1995

[54] SURFACE-ACTIVE COMPOUNDS BASED ON MODIFIED CASTOR OIL FATTY SUBSTANCES

[75] Inventors: Heinz Uhrig, Steinbach/Taunus; Albert Münkel, Liederbach, both of Germany

[73] Assignee: Hoechst AG, Frankfurt, Germany

[21] Appl. No.: 105,378

[22] Filed: Aug. 11, 1993

[30] Foreign Application Priority Data

Aug. 11, 1992 [DE] Germany .................... 42 26 504.5

[51] Int. Cl.⁶ ............................................. C07C 53/00
[52] U.S. Cl. ........................................ 554/96; 554/97; 554/213; 554/215; 554/227
[58] Field of Search ................. 554/96, 97, 213, 215, 554/227

[56] References Cited

U.S. PATENT DOCUMENTS

| | | | |
|---|---|---|---|
| 1,779,367 | 10/1930 | Bruson | 528/301 |
| 1,785,930 | 12/1930 | Bradley | 528/295.5 |
| 1,978,533 | 10/1934 | Holt | 524/26 |
| 2,027,467 | 1/1936 | Brubaker et al. | 554/116 |
| 2,107,610 | 2/1938 | Hovey | 528/274 |
| 2,153,511 | 4/1939 | Cheetham et al. | 528/286 |
| 3,560,419 | 2/1971 | Crovatt et al. | 524/710 |
| 4,371,683 | 2/1983 | Fock et al. | 528/60 |
| 4,597,906 | 7/1986 | Uhrig et al. | 554/90 |
| 5,008,442 | 4/1991 | Uhrig et al. | 560/149 |

FOREIGN PATENT DOCUMENTS

77/21701 3/1978 Australia .
1532506 11/1978 United Kingdom .

*Primary Examiner*—José G. Dees
*Assistant Examiner*—Dwayne C. Jones
*Attorney, Agent, or Firm*—Connolly and Hutz

[57] ABSTRACT

The demands on the properties of pigments, in particular in the fields of emulsion paints and printing inks, which constantly become more specific have made it necessary to develop selective and environmentally friendly dispersing, emulsifying and coupling auxiliaries.

The compounds according to the invention are esterification and/or arylation products prepared from natural or modified castor oil or ricinoleic acids, which products are alkoxylated and, if desired, linked by esterification with dicarboxylic acids to give recurring structural units. If desired, the terminal hydroxyl groups of these modified alkoxylates of castor oil fatty substances have been esterified with fatty acids, aromatic carboxylic acids and/or resin acids and any free hydroxyl groups which may be present have preferably been reacted with dicarboxylic acids and sulfite to give the corresponding monoesters containing anionic radicals.

The compounds according to the invention are suitable for a wide range of applications in the field of surface-active agents, for example in the preparation of azo pigments, emulsion paints and printing inks, for improving the coloristic and rheological properties. The compounds according to the invention are particularly compatible with the environment owing to their biodegradability.

12 Claims, No Drawings

SURFACE-ACTIVE COMPOUNDS BASED ON MODIFIED CASTOR OIL FATTY SUBSTANCES

The invention is in the field of surface-active agents.

In the production of dispersions and preparations of colorants, for example disperse dyes, but preferably inorganic and organic pigments, for applications in aqueous and organic media, a multiplicity of nonionic, anionic and also cationic surfactants are used. The type of surfactants has a substantial effect on the fine dispersion and thus on the color strength of the colorants in the particular application media. Moreover, the type of surfactants exerts a decisive influence on viscosity, gloss and shelf life. Surfactants are usually also used in the preparation of azo dyes from sparingly soluble coupling components, in which they permit good distribution of the coupling component in the reaction medium and complete reaction during the azo coupling. Likewise, the coloristic properties in the various application media in the field of printing inks are substantially affected by the surface-active properties of such surfactants. Furthermore, anionic, cationic and amphoteric auxiliaries, such as, inter alia, various amines, amine resins, modified protein hydrolysates and condensation products of polyacids with amines are used, in addition to known neutral salts of synthetic auxiliaries, for example, for the dyeing of leather (Ullmann, Encyklopädie der technischen Chemie (Encyclopedia of Industrial Chemistry), 4th Ed., 1978, Volume 16, page 150).

AU 77/21,701 discloses nonionic surface-active agents as solubilizers, which are obtained by ethoxylation of natural castor oil or hydrogenated castor oil.

According to GB-A-1,532,506 phenyl-, tolyl- and benzyl-modified castor oil ethoxylates are used for the preparation of emulsion concentrates of water-insoluble biocides.

According to U.S. Pat. No. 4,597,906 and U.S. Pat. No. 5,008,442, water-soluble surface-active compounds based on arylated fatty substances are prepared as coupling auxiliaries for azo pigments and as dispersing agents for disperse dyes.

U.S. Pat. No. 4,371,683 also mentions castor oil, in addition to aliphatic polyalkylene oxide derivatives and polystyrenes, for the preparation of curable adhesives.

U.S. Pat. Nos. 1,779,367, 2,107,610 and 2,153,511 describe alkyd resins based on natural and modified castor oils containing succinic acid, phthalic acid and glycerol.

Furthermore, in U.S. Pat. No. 3,560,419, phosphoric esters with additional use of castor oil ethoxylates are mentioned as viscose additives and spin finishes for the production of polyamide staple fibers.

Textile auxiliaries, such as, for example, wetting, dyeing and mercerization auxiliaries based on low- and high-sulfated or sulfonated castor oils and ricinoleic monoesters are described as Turkish Red oils, Monopole soaps and Prestabit oils in Lindner, "Tenside, Textilhilfsmittel und Waschrohstoffe" (Surfactants, Textile Auxiliaries and Detergent Base Materials), 2nd Edition, 1964, Volume 1, page 624 to 633.

However, none of the products described in the abovementioned publications is suitable for achieving a decisive improvement in the flowability of printing inks and the flocculation stability of exterior paints without adversely affecting other parameters, such as color strength, gloss, hue and dispersibility.

The object of the present invention was to provide surface-active agents which are suitable for the preparation of readily flowable solid dispersions which are resistant to flocculation, preferably colorant dispersions, for exterior painting and are substantially free of the abovementioned disadvantages.

The present invention relates to novel compounds based on a castor oil or a ricinoleic acid, composed of a) 1 to 10, preferably 1 to 5, divalent to nonavalent units of the formula (Ia)

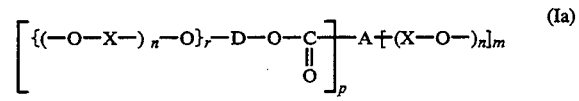

b) 1 to 72, preferably 1 to 23, in particular 2 to 9, monovalent radicals of the formula (Ib)

and, in the case where two or more units of the formula (Ia) are present, additionally of c) 1 to 9, preferably 1 to 4, divalent groups of the formula (Ic)

$$-CO-E-CO- \qquad (Ic),$$

each of the free valences shown in formula units (Ia) being defined such that each, independently of the others, is directly linked to a formula unit (Ib) or a valence of the formula unit (Ic), and, in formula units (Ia) to (Ic)

A being the radical of a natural or modified castor oil or the radical of a natural or modified ricinoleic acid;

D being a direct bond or a divalent radical of a straight-chain or branched di- or hexahydric alcohol having 2 to 8 carbon atoms or a divalent radical of an alkylolamine

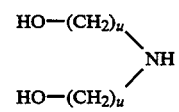

or

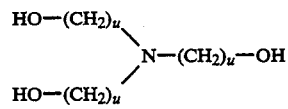

in which a is an integer from 0 to 4, u and v are identical or different and are an integer from 2 to 14, preferably 2 to 3, each or a portion of the OH, NH or NH$_2$ groups being alkoxylated;

E being a straight-chain or branched or cyclic aliphatic radical having 0 to 20, preferably 1 to 10, carbon atoms; an aromatic radical having 6 to 10 carbon atoms; an alkenyl radical based on a dimerized unsaturated C$_{28}$-C$_{72}$-fatty acid; or a group of the formulae —CH=CH—, —CH$_2$CH(SO$_3$M)— or —CH(SO$_3$M)CH$_2$—, in which M is a cation or a radical of the formula —(X—O—)$_n$H;

X being a group of the formulae —CH$_2$CH$_2$—, —CH(CH$_3$)CH$_2$ and —CH$_2$CH(CH$_3$)— or a combination thereof;

Z being identical or different radicals $Z^1$ to $Z^6$, in which $Z^1$ is hydrogen, $Z^2$ is an acyl radical of the formula $R^1$—CO— in which $R^1$ is a phenyl, naphthyl or hydroxynaphthyl radical, $Z^3$ is an acyl radical of an unmodified or modified natural resin acid, $Z^4$ is an acyl radical of a di- or tricarboxylic acid based on a di- or trimerized $C_{28}$-$C_{72}$-fatty acid or an acyl radical of a saturated or unsaturated $C_8$-$C_{22}$-fatty acid, radicals $Z^5$ are identical or different radicals of the formulae —CO—$(CH_2)_q$—COOM, —CO—CH=CH—COOM, —CO—$CH_2$CH($SO_3$M)—COOM, —CO—CH($SO_3$M)—$CH_2$-COOM and —OC—$C_6H_4$—COOM, in which q is an integer from 0 to 10, $Z^6$ is —$SO_3$M, in which M is hydrogen; an alkali metal; one equivalent of an alkaline earth metal; an oxyalkyl radical of the formula $(X-O-)_nH$; an ammonium group which is unsubstituted or substituted by one to four $C_1$-$C_5$-alkyl radicals or one to four $C_2$-$C_5$-alkylol radicals; an ammonium group obtained from ammonia or from $C_1$-$C_5$alkylamines or $C_2$-$C_5$-alkylolamines by an addition reaction with 1 to 150, preferably 5 to 30, ethylene oxide or propylene oxide units or a combination of ethylene oxide and propylene oxide units; or a group of the formula (II)

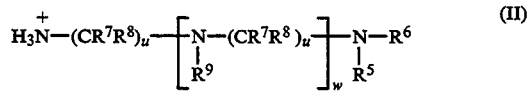

in which $R^9$, $R^5$ and $R^6$ are identical or different and are a hydrogen atom or a hydroxyalkyl group having 1 to 6 carbon atoms, preferably 2 to 3 carbon atoms, and $R^7$ and $R^8$ are identical or different and are hydrogen or methyl, each u is identical to or different from the others and is an integer from 2 to 14, preferably 2 to 3, and w is an integer from zero to 25, preferably from zero to 5; or in which M is a group of the formula (III)

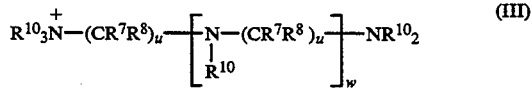

in which $R^{10}$ is the group H—$(O-X-)_p$, in which X has the abovementioned meanings and y is an integer from 1 to 100, preferably 1 to 30, m, in the case where A is a ricinoleic acid radical, being a number from 1 to 3, and, in the case where A is a castor oil radical, being a number from 1 to 9, n being a number from 1 to 250, preferably 5 to 125, particularly preferably 10 to 80, p, in the case were A is a castor oil, being the number 0, and, in the case where A is a ricinoleic acid radical, being the number 1, and r being a number from 1 to 6, preferably 1 to 4, and at least one radical Z being a radical from the group $Z^2$, $Z^3$, $Z^4$ and $Z^5$; or at least two units of the formula (Ia) being linked to one another via a divalent group of the formula (Ic) and Z having the meaning of $Z^1$ to $Z^6$.

A modified castor oil is understood to mean a mono- or polyhydrogenated or a mono- or polyarylated castor oil. A modified ricinoleic acid is understood to mean a hydrogenated or arylated ricinoleic acid. In this context, "arylated" means that a phenolcarboxylic acid, preferably a hydroxynaphthoic acid or a derivative thereof, has been added to an olefinic double bond of the castor oil fatty substance.

"Castor oil fatty substance" is understood to mean natural or modified castor oil or natural or modified ricinoleic acid.

Of particular interest according to the invention are those compounds containing 1 to 5 units of the formula (Ia), in which A is the radical of a natural or modified castor oil and p is therefore the number 0, X is —$CH_2CH_2$— and n is an integer from 5 to 125, preferably 10 to 80.

Of particular interest are furthermore those compounds containing 1 to 5 units of the formula (Ia), in which A is the radical of a natural or modified ricinoleic acid, p is the number 1 and m is a number from 1 to 3, D is a divalent radical of a straight-chain or branched di- to hexahydric alcohol having 2 to 6 carbon atoms or of a $C_2$-$C_3$-alkylolamine, $C_2$-$C_3$-alkylol-$C_2$-$C_3$-alkylenediamine, $C_2$-$C_3$-alkylol-di-$C_2$-$C_3$-alkylenetriamine or $C_2$-$C_3$-alkylol-tri-$C_2$-$C_3$-alkylenetetramine, X is —$CH_2CH_2$— and n is an integer from 5 to 125, preferably 10 to 80.

Of particular interest are furthermore those compounds according to the invention which contain 2 to 9 monovalent radicals of the formula (Ib), in which the radicals Z are identical or different radicals of the formulae $Z^2$, $Z^3$, $Z^4$ and $Z^5$, preferably $Z^3$ and $Z^5$.

Of particular interest are furthermore those compounds according to the invention which contain 1 to 4 divalent groups of the formula (Ic), in which E is a straight-chain, branched or cyclic aliphatic alkylene radical having 2 to 10 carbon atoms, preferably ethylene, butylene, pentylene, hexylene and decylene; a phenylene radical; or a group of the formulae —CH=CH—, —$CH_2$CH($SO_3$M)— or —CH($SO_3$M)$CH_2$—, in which M is a cation.

The present invention also provides a process for the preparation of the compounds according to the invention, which comprises a1) either esterifying a castor oil fatty substance partially or completely with at least one acid on which the acyl radicals $Z^2$, $Z^3$, $Z^4$, $Z^5$, $Z^6$ and —CO—E—CO— are based or a reactive derivative of this acid, the ester obtained containing at least one free hydroxyl group, a2) or arylating a castor oil fatty substance with at least one hydroxynaphthoic acid on which the acyl radical $Z^2$ is based or a derivative, preferably an amide, of a hydroxynaphthoic acid at one or more olefinic double bonds, or carrying out esterification according to a1) and arylation according to a2) at the same time;

b) then alkoxylating the free hydroxyl groups or carboxyl groups of the compounds obtainable by a1) or a2) with ethylene oxide or propylene oxide or both epoxides in succession or a mixture of both epoxides;

c) then, if desired, esterifying the alkoxylates obtained by b) partially or completely with C1) at least one carboxylic acid on which the acyl radicals $Z^2$, $Z^3$, $Z^4$, $Z^5$ and —CO—E—CO— are based or a reactive derivative of this carboxylic acid, preferably an anhydride, or subjecting them to mixed esterification with a plurality of the abovementioned carboxylic acids or reactive derivatives thereof, c2) and reacting any maleic monoester groups present, if desired, with a sulfite or with sulfurous acid c3) or sulfating the alkoxylates obtained by b) with a sulfating agent on which the radical $Z^6$ is based, preferably sulfuric acid, chlorosulfonic acid, sulfamic acid or sulfur trioxide; and d) in the case where in c) a radical of the formula $Z^5$ or $Z^6$ has been introduced, converting, if desired, the product into the corresponding salt or alkoxylate with a base on which the radical M is based.

In an alternative embodiment of the process according to the invention, the reaction step a) is omitted, and the castor oil fatty substance is first alkoxylated according to reaction step b) and the resulting alkoxylate is then further reacted in accordance with reaction steps c) and d).

In the case where the starting material used is a natural or modified ricinoleic acid, it is advantageous to esterify the free carboxyl group of ricinoleic acid by a di- to hexahydric alcohol on which the radical D is based or an alkylolamine. It is advantageous to carry out said esterification before the alkoxylation step b). Of particular interest for the esterification of the free carboxyl groups of ricinoleic acid are: glycerol, diglycerol, polyglycerols, 1,2,4-butanetriol, 1,4-butanediol, glycol, polyglycols, 1,1,1-trimethylolethane, 1,1,1-trimethylolpropane, pentaerythritol, 2,4-dihydroxy-3-methylolpentane, hexanetriol, sorbitol, anhydrosorbitol, hexitol or mannitol and mono-, di- and triethanolamine and furthermore alkylolamines, such as N-(2-hydroxyethyl)-1,2-diaminoethane, N-(2-hydroxyethyl)diethylenetriamine, N-(2-hydroxyethyl)triethylenetetramine and 2-aminoethanol.

Esterification with the polyhydric alcohols or alkylolamines mentioned takes place in an alcohol or alkylolamine/ricinoleic acid molar ratio of 1:1 to 4:1, preferably 1:1 to 2:1, at a temperature of 180° to 300° C., preferably at 200° to 270° C., if appropriate with the addition of an entrainer, for example of an aromatic hydrocarbon or chlorohydrocarbon. Examples of catalysts which can be used are benzenesulfonic acid, p-toluenesulfonic acid, boric acid, tin powder or sulfuric acid. Tin powder is used in an amount of 1 to 4 % by weight, the other acids mentioned are used in an amount of 0.1 to 2% by weight, preferably 0.5 to 1% by weight, in each case relative to the compound to be reacted.

The castor oil fatty substance on which group A is based is, for example, commercially available castor oil comprising essentially a glyceride of ricinoleic acid, oleic acid, linoleic acid and stearic acid, or is a monomor polyhydrogenated castor oil, hydrogenated ricinoleic acid or a castor oil which is mono- or polyarylated with the hydroxynaphthoic acids mentioned below under a2) or derivatives of the hydroxynaphthoic acids or is monoarylated ricinoleic acid. Natural castor oil contains free hydroxyl groups and olefinic double bonds.

Examples of aromatic carboxylic acids on which the acyl radical $Z^2$ is based are benzoic acid, 1-naphthoic acid or 2-naphthoic acid and hydroxynaphthoic acids, preferably 1-hydroxy-4-naphthoic acid, 2-hydroxy-1-naphthoic acid, 3-hydroxy-1-naphthoic acid, 5-hydroxy-1-naphthoic acid, 6-hydroxy-1-naphthoic acid, 7-hydroxy-1-naphthoic acid, 8-hydroxy-1-naphthoic acid, 1-hydroxy-2-naphthoic acid, 3-hydroxy-2-naphthoic acid, 5-hydroxy-2-naphthoic acid, 6-hydroxy-2-naphthoic acid, 7-hydroxy-2-naphthoic acid and 1-hydroxy-3-naphthoic acid.

The resin acids on which the acyl radical $Z^3$ is based are natural or modified resin acids, for example abietic acid, dehydroabietic acid, dihydroabietic acid, tetrahydroabietic acid, levopimaric acid, dextropimaric acid and isodextropimaric acid, such as are present in commercially available rosin types, furthermore disproportionated, hydrogenated and dimerized resin acids.

The fatty acids on which the acyl radical $Z^4$ is based are dimerized or trimerized fatty acids having 28 to 72, in particular 36 to 54, carbon atoms, and saturated or unsaturated $C_8$–$C_{22}$-fatty acids, for example octanoic acid, pelargonic acid, capric acid, undecanoic acid, lauric acid, tridecanoic acid, myristic acid, pentadecanoic acid, palmitic acid, heptadecanoic acid, stearic acid, nonadecanoic acid, arachidic acid, behenic acid, 10-undecenoic acid, lauroleic acid, myristoleic acid, palmitoleic acid, 6c- and 6t-octadecenoic acid, elaidic acid, oleic acid, linoleic acid and linolenic acid, in particular even-numbered fatty acids or hydroxy fatty acids each having 8 to 20 carbon atoms, for example the corresponding abovementioned even-numbered fatty acids and in particular mixtures thereof obtained from natural products, such as tall oil fatty acid, tallow fatty acid, coconut oil fatty acid, palm kernel oil fatty acid and linseed oil fatty acid, preferably the fatty acids mentioned containing 12 to 18 carbon atoms.

Examples of acids or carboxylic anhydrides on which the acyl radical $Z^5$ is based are maleic acid, maleic anhydride, fumaric acid, phthalic acid, phthalic anhydride, isophthalic acid, terephthalic acid, oxalic acid, malonic acid, succinic acid, succinic anhydride, glutaric acid, glutaric anhydride, adipic acid, pimelic acid, suberic acid, azelaic acid, sebacic acid and sulfosuccinic acid, preferably succinic acid, phthalic acid, terephthalic acid, maleic acid and fumaric acid, in particular sulfosuccinic acid.

a1) Esterification of the hydroxyl groups of the abovementioned castor oils and ricinoleic acids with the carboxylic acids on which the acyl radicals $Z^2$, $Z^3$, $Z^4$ and $Z^5$ are based takes place in a castor oil fatty substance/carboxylic acid (anhydride) molar ratio of 1:1 to 1:9, preferably 1:1 to 1:4 and is carried out by esterification methods customary per se. The reaction temperature to be maintained is usually between 20° C. and 240° C. depending on the esterification method. In order to increase the yield, esterification is preferably carried out in an inert organic solvent which is suitable as entrainer for removing the water of reaction. For example, esterification can be carried out in xylene as the organic solvent and in the presence of acid catalysts at a temperature of 130° to 220° C. Examples of suitable acid catalysts are acids and Lewis acids, such as benzenesulfonic acid, p-toluenesulfonic acid, boric acid, tin powder, zinc chloride or sulfuric acid in the abovementioned concentrations.

If the abovementioned castor oils and ricinoleic acids are esterified with a dicarboxylic acid on which the acyl radical —OC—E—CO— is based, 2 to 10, preferably 2 to 5, castor oil or ricinoleic acid units, which, if desired, are partially esterified with one or more radicals $Z^2$, $Z^3$, $Z^4$ or $Z^6$, can be linked to one another by groups of the formula —OC—E—CO—. The esterification resulting in linkage is carried out with one or more dicarboxylic acids of the formula HOOC—E—COOH in a castor oil fatty substance/dicarboxylic acid molar ratio of 2:1 to 10:9, preferably 2:1 to 5:4. Dicarboxylic acids suitable for linkage are preferably aliphatic dicarboxylic acids having 3 to 12 carbon atoms, in particular malonic acid, succinic acid, glutaric acid, adipic acid, 1,5-pentanedicarboxylic acid, 1,6-hexanedicarboxylic acid or 1,10-decanedicarboxylic acid, but also, for example, cyclohexane-1,4-dicarboxylic acid and aromatic dicarboxylic acids, such as phthalic acid or terephthalic acid, and dimerized unsaturated $C_{28}$–$C_{72}$-fatty acids. Instead of the dicarboxylic acids, anhydrides, for example maleic anhydride, succinic anhydride or phthalic anhydride and reactive dicarboxylic acid derivatives, for example in the case of transesterification reactions alkyl esters of the dicarboxylic acids mentioned, can also be used for esterification.

It is also possible to esterify partially esterified or linked castor oil fatty substances further with the carboxylic acids or anhydrides on which the acyl radicals $Z^2$, $Z^3$, $Z_4$ and $Z^5$ are based. This esterification takes place by known methods at temperatures of 130° to 220° C., preferably at 150° to 180° C., in the presence of inorganic or organic acids or of Lewis acids, such as zinc chloride, benzenesulfonic acid, p-toluenesulfonic acid, boric acid, tin powder or sulfuric acid in the abovementioned concentrations. The resulting water of reaction is removed by distillation, if appropriate with the addition of an entrainer, for example of a hydrocarbon or chlorohydrocarbon. If dicarboxylic anhydrides are used, monoesterification takes place at a temperature as low as 0° to 150° C., preferably 40° to 120° C., if appropriate in the presence of alkali metal hydroxides, the concentration of the alkali metal hydroxides being 0.1 to 1.0% by weight, relative to the total mixture. In the case of maleic anhydride, succinic anhydride and phthalic anhydride, it is advantageous, owing to the tendency to sublimation, to carry out the reaction in pressure vessels under a superatmospheric pressure of 0.2 to 1.0 bar of nitrogen or air and to provide for vigorous mixing, since at the beginning of the reaction the melted anhydrides are always slightly miscible with the various castor oil compounds.

a2) Arylation of the olefinic double bonds of the abovementioned castor oils and ricinoleic acids is carried out with the abovementioned hydroxynaphthoic acids, preferably with 2-hydroxy-1-naphthoic acid, 3-hydroxy-1-naphthoic acid, 1-hydroxy-2-naphthoic acid, 3-hydroxy-2-naphthoic acid and 1-hydroxy-3-naphthoic acid, or with hydroxynaphthoic acid derivatives, for example with the anilide, o-toluidide, o-anisidide, p-anisidide, 4-methoxy-2-toluidide or β-naphthylamide of 2-hydroxy-3-naphthoic acid, and with methyl β-hydroxynaphthoate and phenyl 1-hydroxy-2-naphthoate. Arylation is carried out by methods customary per se in the presence of strongly acidic catalysts, for example Lewis acids, such as boron trifluoride or aluminumchloride, p-toluenesulfonic acid, methanesulfonic acid, mineral acids or ion exchangers at temperatures of between 50° and 200° C., preferably 120° to 160° C., if appropriate in an organic medium, 0.9 to 3 mol, preferably 1 to 2 mol, of a hydroxynaphthoic acid or a derivative thereof being used per mole of castor oil or ricinoleic acid. The acids are used in the abovementioned concentration ranges, and the ion exchangers are used in amounts of 5 to 30, preferably 5 to 10, % by weight, relative to the compound to be reacted.

b) Alkoxylation of the castor oils or ricinoleic acids mentioned, of the esterification and arylation products and of the compounds obtainable by linkage of two or more structural units of the formula (Ia) is carried out by customary methods, preferably with alkali metal hydroxides or alkali metal alkoxides as catalysts at 100° to 200° C., preferably at 140° to 180° C. The amount of ethylene oxide and/or propylene oxide is such that the alkoxylates are emulsified with the formation of a stable emulsion or are completely dissolved in water. Preferably, the amount of ethylene oxide and/or propylene oxide which adds to each free carboxyl and hydroxyl group is in each case 1 to 250, preferably 5 to 125, in particular 10 to 80, mol. The amount of alkylene oxide added is also determined by the intended purpose and thus the desired degree of hydrophilicity.

Preferred alkali metal hydroxides are potassium hydroxide or sodium hydroxide, and preferred alkali metal alkoxides are sodium methoxide or sodium ethoxide; at the beginning of alkoxylation, the concentration of the catalyst is preferably 0.05 to 2.0% by weight, relative to the compound to be alkoxylated. Alkoxylation can be carried out under atmospheric pressure or in pressure vessels at 1 to 10, preferably 2 to 4, bar with propylene oxide or, preferably, ethylene oxide or mixtures of both, the alkylene oxide being introduced in gaseous or liquid form. If desired, the reaction mixture is neutralized after alkoxylation is complete, for example with acetic acid.

Linkage of two or more of the abovementioned alkoxylated compounds with groups of the formula —CO—E—CO— (Ic) can be carried out in one or two reaction steps by esterification with the abovementioned dicarboxylic acids or anhydrides thereof, an alkoxylate/dicarboxylic acid ratio of 2:1 to 10:9 being preferred. In the case where only one free hydroxyl group is left in a partially esterified alkoxylate, a molar ratio of 2:1 is appropriate.

c1) If desired, the free terminal hydroxyl groups of the alkoxylated castor oil or ricinoleic acid compounds are partially or completely esterified with at least one carboxylic acid on which the acyl radicals $Z^2$, $Z^3$, $Z^4$, $Z^5$ and —OC—E—CO— are based or its anhydride in one, two or three further reaction step(s), the carboxylic acid (anhydride)/alkoxylate molar mass ratios being 1:1 to 9:1, preferably 1:1 to 4:1.

Esterification of the alkoxylated castor oil or ricinoleic acid compounds with the aromatic carboxylic acids, natural or modified resin acids or simple, di- or trimerized fatty acids is carried out by esterification methods customary per se. The reaction temperature is usually between 20° C. and 240° C., depending on the esterification method. In order to increase the yield, esterification is preferably carried out in an inert organic solvent which is suitable as entrainer for removing the water of reaction. Esterification is preferably carried out in xylene as the organic solvent and in the presence of an acid catalyst at a temperature of 130° to 220° C. Acids and Lewis acids, such as benzenesulfonic acid, p-toluenesulfonic acid, boric acid, tin powder, zinc chloride and sulfuric acid can be used in the abovementioned concentration ranges as acid catalysts.

Esterification of the alkoxylated castor oil or ricinoleic acid compounds or partial esterification products thereof with the aromatic carboxylic acids or resin acids mentioned can, alternatively, also be carried out by transesterification using the corresponding alkyl esters, preferably methyl esters, of the acids mentioned in the presence of 0.1 to 1.0 mol equivalents of alkali metal alkoxide, preferably sodium methoxide, at 150° to 200° C., preferably 160° to 190° C., while distilling off the released alkanol, preferably methanol.

To prepare mixed esters, a mixture of resin acids, fatty acids and/or aromatic carboxylic acids or reactive derivatives thereof can be used, or esterification is carried out via at least two successive partial esterification steps.

The novel nonionic aromatic carboxylic esters, resinic esters or fatty acid esters of the alkoxylated castor oil fatty substances are as such useful surface-active agents and can be used in accordance with the invention.

To introduce anionic ester groups, the dicarboxylic acids and anhydrides used according to the invention are those on which the radical $Z^5$ is based.

In the case of the anhydrides, esterification takes place by mixing and thoroughly stirring them with the alkoxylated castor oil fatty substances at 10° to 120° C., preferably at 40° to 80° C., in the presence of alkali metal hydroxides. Advantageously, the alkali metal hydroxide concentration is 0.1 to 1.0% by weight, relative to the total mixture. In the case of maleic anhydrides, it is advantageous, owing to the tendency to sublimation, to carry out the reaction in pressure vessels at a super-atmospheric pressure of 0.2 to 1.0 bar of nitrogen or air and to provide for vigorous mixing, since at the beginning of the reaction the molten maleic anhydride shows poor miscibility with the partially esterified alkoxylates.

c2) In the case where maleic monoester groups have been introduced, it is furthermore advantageous to convert these monoester groups into the corresponding sulfosuccinic monoester groups. This can be achieved, for example, by addition of aqueous solutions of sulfites or bisulfites to the compounds containing maleic monoester groups. 1.0 to 1.5, preferably 1.0 to 1.1, mol of sulfurous acid are used in the form of alkali metal sulfites or alkylene earth metal sulfites or alkali metal bisulfites or alkaline earth metal bisulfites or alkali metal pyrosulfites or alkaline earth metal pyrosulfites per mole of maleic monoester group. The reaction is usually carried out in the presence of about 50 to 85% by weight of water, relative to the total solution or mixture. The amount of water depends on the solubility of the underlying sulfosuccinic monoester salts and on the viscosity of the solutions. The reaction temperature in the reaction of sulfites with the maleic monoester compounds is usually 20° to 100° C., in particular 40° to 80° C.

c3) In order to introduce $SO_3H$ groups, the alkoxylates obtainable by b) are reacted with 1 to 9 mol, preferably 1 to 4 mol, of a sulfating agent, for example sulfuric acid, sulfamic acid or chlorosulfonic acid or suitable anhydrides, per mole of alkoxylate. While sulfation with sulfamic acid results in the formation of the ammonium salts of the sulfuric monoesters, the embodiment which uses gaseous sulfur trioxide in mixtures with inert gas and also sulfation with chlorosulfonic acid lead to sulfuric monoesters in the acid form, from which salts can be prepared according to d) by neutralization with suitable inorganic or organic bases. For this neutralization, it is preferred to use alkali metal hydroxides, which lead to the readily water-soluble alkali metal salts of the sulfuric monoesters according to the invention.

The invention also provides those embodiments in which one or more alkoxylation steps analogously to reaction step b) and, if desired, one or more esterification steps analogously to reaction step c) are carried out following reaction step c).

d) The alkoxylated castor oil fatty substances esterified according to c) are advantageously neutralized with 1 to 9, preferably 1 to 4, mol of a base on which M is based per mole of the castor oil fatty substances from c), in particular with amines of the formulae (II) or (III). The reaction to give the amine salts is carried out at a temperature of 20° to 130° C., preferably at 40° to 90° C., in particular at 70° to 80° C. Examples of suitable amino compounds are 1,2-diaminoethane, 1,3-diaminopropane, 1,2-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,12-diaminododecane, diethylenetriamine, dipropylenetriamine, triethylenetetramine, dipropylenetetramine, tetraethylenepentamine, tetrapropylenepentamine, pentaethylenehexamine, pentapropylenehexamine, hexaethyleneheptamine, hexapropyleneheptamine, heptaethyleneoctamine, heptapropyleneoctamine, 1,3-diamino-2,2-dimethylpropane, 1,2-diamino-2-methylpropane, 1,3-diamino-2-methylpropane, 2,5-diamino-2,5-dimethylhexane, N-(2-aminoethyl)-1,3-propylenediamine and N,N'-bis(3-aminopropyl)ethylenediamine.

While sulfites are particularly suitable for forming the dialkali metal salts of sulfosuccinic monoesters, the addition reaction of bisulfites allows the degree of hydrophilicity to be influenced additionally by neutralization with bases. Suitable bases are ammonia, $C_1$–$C_5$-alkylamine, $C_2$–$C_5$-alkylolamines, amines of the formula (II) or (III) or alkylene oxide adducts thereof, up to about 150 mol of ethylene oxide or propylene oxide or both alkylene oxides having been combined therewith per mole of amine or alkylolamine and up to 150, preferably 5 to 30, molecules of ethylene oxide or propylene oxide or both having been combined therewith per reactive hydrogen atom of the amines mentioned. Amines or alkylolamines which are of particular interest are ethylamine, propylamine, isopropylamine, butylamine, isobutylamine, monoethanolamine, monopropanolamine, monoisopropanolamine, monobutanolamine, monoisobutanolamine, diethanolamine, dipropanolamine, dibutanolamine, triethanolamine, tripropanolamine or tributanolamine and di- and polyamines, such as ethylenediamine, ethylenetriamine, triethylenetetramine, propylenediamine, dipropylenediamine, dipropylenetriamine or tripropylenetetramine.

Owing to the multiplicity of reaction centers in the starting compounds, the preparation of the compounds according to the invention does not yield a pure, uniform end product but a mixture which, however, contains the compounds according to the invention as the main component, that is in an amount of more than 50% by weight, preferably in an amount of more than 90% by weight.

The process according to the invention produces mixtures in particular in those cases where an alkoxylate obtainable by reaction step c) is esterified in a single reaction step with a plurality of different carboxylic acids. If the dicarboxylic acids are also present in this esterification, mixtures of bridged and non-bridged alkoxylate esters are usually obtained.

The molecular weight of the compounds according to the invention can vary within a wide range and ranges from 800 to 20,000, preferably 2,000 to 10,000, in particular 1,000 to 5,000.

The compounds according to the invention are yellowish or greenish, low-foaming surface-active substances, which surprisingly are suitable for the preparation of readily flowable and stable solid dispersions, in particular of readily flowable pigment preparations which are resistant to flocculation.

The compounds according to the invention exhibit versatile advantageous properties. They belong to the class of surface-active compounds in accordance with DIN (German Standard Specification) 53900, lower the surface tension as measured by the ring detachment method (DIN (German Standard Specification) 53914) and, according to the results in the modified Ross-Miles test (DIN (German Standard Specification) 53902), are to be designated as non-foaming or low-foaming surface-active substances. At a suitable degree of hydrophilization, they show excellent wetting power for cotton by the dip-wetting method (DIN (German Standard Specification) 53901) in combination with good leveling behavior in accordance with DIN (German Standard Specification) 53504. They possess very good flocculation-preventing power towards pigments and dyes (DIN (German Standard Specification) 53908) and a very good water-distributing effect as cleaning promoter (DIN (German Standard Specification) 53980) and good washability as lubricant (DIN (German Standard Specification) 53504). The compounds according to the invention are biodegradable and thus particularly environment-friendly.

Owing to their versatile surface-active properties, the compounds according to the invention can be used for a broad spectrum of applications.

Accordingly, the invention also relates to the use of a compound according to the invention as surface-active agent. Of particular interest is the use as dispersing and distributing agent for the fine dispersion and stabilization of inorganic and organic pigments, in particular of sparingly soluble and insoluble colorants, preferably for the preparation of readily flowable pigment dispersions for aqueous emulsion paints and for the aqueous printing ink sector. Of further interest is the use for the preparation of tanning agent dispersions based on metal salts for the dyeing and pigmenting of leather or for the preparation of disperse dyes, such as are preferably used for the dyeing of natural and synthetic fiber materials, such as cotton, wool, cellulose, staple viscose, cellulose acetate, cellulose triacetate, polyester, polyamide and polyacrylonitrile, or of fiber materials containing these substances.

The compounds according to the invention are also suitable for use as coupling auxiliary and preparing agent in the preparation of azo colorants, in particular of azo pigments, and as additives and emulsifiers, for example as anticorrosive additives, as additives for the preparation of cleaning promoters, carrier emulsions, emulsions of mineral oils and fatty substances, metalworking agents and anticorrosives and of formulations for crop protection and pest control agents. Furthermore, they are suitable as wetting, leveling, flotation agents, viscose additives, viscose finishing agents and dyeing auxiliaries and wetting-back auxiliaries for textiles and leathers.

The compounds according to the invention can be used individually or as mixtures and in combination with other, nonionic and, if desired, with anionic or cationic surfactants or mixtures thereof. Furthermore, they can be used together with customary amounts of builders or other customary additives or auxiliaries in formulations of emulsifying and dispersing agents.

In the examples which follow, parts (p.) and percentages are by weight, and parts by volume relate to parts by weight as the liter relates to the kilogram. The degree of conversion in the particular reaction steps is characterized in the preparation examples by the determination of the hydroxyl number, acid number and amine number. The acid number (AN) is determined by DIN (German Standard Specification) 53402. The acid number indicates the amount of potassium hydroxide in milligrams consumed for neutralizing 1 g of the reaction product. The hydroxyl number is determined by DIN (German Standard Specification) 53240 and is a measure of the free hydroxyl group content in the molecule; it corresponds to the amount of potassium hydroxide in mg necessary for neutralizing the amount of acetic acid consumed by acetylation of 1 g of the test substance. The amine number is determined by DIN (German Standard Specification) 53176 and is the amount of potassium hydroxide in milligrams equivalent to the amine content of 1 g of substance.

PREPARATION EXAMPLE 1 a) Castor oil rosin ester 466 p. of commercially available castor oil are heated together with 151 p. of disproportionated rosin to 70° to 80° C. and stirred for one hour under nitrogen gas. After addition of 12 parts of tin powder, 4.0 parts of p-toluenesulfonic acid and 150 parts by volume of xylene, the mixture is heated at 150° to 160° C. for 16 hours, and the water of reaction is removed by azeotropic distillation. After the xylene has been distilled off, the product obtained has an acid number of less than 25.

b) Castor oil rosin ester ethoxylate 200 p. of castor oil rosin ester according to Preparation Example 1a) are heated in a pressure vessel, after addition of 9 p. of sodium methoxide (30% in methanol), to 80° C. to 90° C. with stirring, and the methanol is distilled off under reduced pressure. After increasing the temperature to 150° C. to 170° C., 578 parts of ethylene oxide are injected at a pressure of 4 to 6 bar. The mixture is then stirred at 150° C. to 160° C. for another hour. The wax-like brown castor oil rosin ester ethoxylate obtained contains on average 80 ethyleneoxy units per molecule and has a hydroxyl number of 27.7.

Preparation Example 2

Castor oil rosin ester ethoxylate di-sulfosuccinic monoester 300 p. of castor oil rosin ester ethoxylate according to Preparation Example 1b) are stirred in accordance with the hydroxyl number with 14.5 p. of maleic anhydride at 70° C. to 80° C. in a nitrogen atmosphere for 3 hours. A solution of 18.7 parts of sodium sulfite in 653 parts of water is run in to the maleic monoester product obtained, and the mixture is stirred at 70° C. to 80° C. for a period of between 1 and 2 hours until the reaction mixture has become water-soluble with the formation of a clear solution. The amount of water added with the sodium sulfite solution can be 50 to 85% by weight of the product-containing solution. The main product obtained is a sulfosuccinic monoester in which both polyoxyethylene chains have been reacted at their end groups down to a residual hydroxyl number of 4.

Preparation Example 3 a) Di(rosin) castor oil ester 302 p. of commercially available disproportionated rosin and 466 p. of commercially available castor oil are heated to 80° to 90° C. under nitrogen gas. After addition of 6 p. of tin powder and 2 p. of p-toluenesulfonic acid and 200 parts by volume of xylene, esterification is carried out at 155° to 165° C. for 8 hours while removing the water of reaction by azeotropic distillation. After the xylene has been distilled off, the product has an acid number of 6.4 b) Di(rosin) castor oil ester ethoxylate

After addition of 9 p. of sodium methoxide (30% in methanol), 300 p. of di(rosin) castor oil ester according to Preparation Example 3a) are reacted analogously to Preparation Example 1b) with 859.8 p. of ethylene oxide. The ester ethoxylate obtained contains on average 97.7 ethylene oxide units per molecule and a hydroxyl number of 9.6.

Preparation Example 4

Di(rosin) castor oil ester ethoxylate sulfosuccinate 500 p. of di(rosin) castor oil ester ethoxylate according to Preparation Example 3b) are stirred in accordance with the hydroxyl number with 8.5 p. of maleic anhydride at 70° to 80° C. in a nitrogen stream for 3 hours. A solution of 10.9 p. of sodium sulfite and 964.58 p. of water is run in to the maleic monoester product obtained, and the batch is stirred at 70° to 80° C. for 2 to 3 hours until it has become water-soluble with the formation of a clear solution. The amount of water added with the sodium sulfite solution can be 50 to 85% by weight of the product. The main product obtained is a sulfosuccinic monoester having a residual hydroxyl number of 0.86.

Preparation Example 5 a) Tri(castor oil) maleic ester 200 p. of commercially available hydrogenated castor oil are esterified with 20.8 p. of maleic anhydride at 75° to 85° C. under nitrogen over a period of 4 hours. The castor oil maleic monoester obtained has an acid number of 61.2. After addition of a further 200 p. of castor oil and 1 part of p-toluenesulfonic acid and 200 parts by volume of xylene, esterification is continued for another 8 to 10 hours while removing the water of reaction by azeotropic distillation at 155° to 165° C. down to an acid number of 10. After a further addition of 220.8 p. of hydrogenated castor oil maleic monoester, esterification is continued at the same temperature for another 5 to 6 hours while removing the water of reaction by azeotropic distillation. The acid number found is 10 to 12. The product obtained contains 3 castor oil units linked to 2 maleic acid units.

b) Tri(castor oil) maleic ester ethoxylate

After addition of 9 p. of sodium methoxide (30% in methanol), 300 p. of tri(castor oil) maleic ester according to Preparation Example 5a) are heated in a pressure vessel to 80° C. with stirring, and the methanol is distilled off under reduced pressure. After increasing the temperature to 150° to 170° C., 348.4 p. of ethylene oxide are injected at a pressure of 4 to 6 bar. Stirring at 150° C. to 160° C. is then continued for another hour. The wax-like brown ethoxylate obtained contains on average 78.3 ethyleneoxy units per molecule and has a hydroxyl number of 43.6.

Preparation Example 6

Tri(castor oil) maleic ester ethoxylate benzoate sulfosuccinate 300 p. of tri(castor oil) ethoxylate according to Preparation Example 5b) are thoroughly mixed at about 20° C. with 28.4 p. of benzoic acid, which corresponds to 2/5 of the hydroxyl number, and the mixture, after addition of 1.5 parts of p-toluenesulfonic acid and 150 parts by volume of xylene, is heated to 150° to 160° C. under a nitrogen atmosphere, the water of reaction being removed by azeotropic distillation over a period of 8 hours. After the entrainer has been distilled off and an acid number of about 5 has been reached, the temperature is lowered to 70° to 80° C., and 22.8 p. of maleic anhydride, which corresponds to 3/5 of the hydroxyl number, and 0.2 part of sodium hydroxide are added, and stirring at the same temperature is continued for another 4 hours.

A solution of 29.4 parts of sodium sulfite in 752 parts of water is run in to the maleic monoester product obtained, and the mixture is stirred at 70° C. to 80° C. over a period of between 1 and 2 hours until the batch has become water-soluble with the formation of a clear solution. The amount of water added with the sodium sulfite solution can be 50 to 85% by weight of the product-containing solution. The main product obtained is a sulfosuccinic monoester in which all 5 polyoxyethylene chains have been reacted at their end group down to a residual hydroxyl number of 7.3.

Preparation Example 7 a) Di(castor oil) maleic ester 300 p. of hydrogenated castor oil are stirred together with 32 p. of maleic anhydride at 70° to 80° C. for 3 hours. After addition of 3 p. of p-toluenesulfonic acid and 200 parts by volume of xylene, the mixture is heated at 135° to 165° C. for 8 hours, and the water of reaction is removed by azeotropic distillation. After the xylene has been distilled off, the product has an acid number of 18. The product obtained contains 2 castor oil units linked by one maleic acid unit.

b) Di(castor oil) maleic ester ethoxylate 200 p. of castor oil maleic ester according to Preparation Example 7a) are reacted, after addition of 1.2 p. of sodium hydroxide, with 573.2 p. of ethylene oxide as described in Preparation Example 1b). The wax-like yellow-brown castor oil ethoxylate obtained contains on average 127.4 ethylene oxide units per molecule and has a hydroxyl number of 22.3.

Preparation Example 8 a) Castor oil rosin ester alkoxylate 200 p. of castor oil rosin ester according to Preparation Example 1a) are introduced as initial charge and reacted at 120° to 140° C. and a pressure of 2 to 4 bar with 162 parts of propylene oxide. After an additional stirring period of 1 hour, 6 parts of sodium methoxide (30% in methanol) are added, the methanol is removed, 184.5 parts of ethylene oxide are introduced at the same temperature and at the same pressure conditions, and the mixture is stirred at 140° to 145° C. and a pressure of 3 to 4 bar for another 2 hours, giving a highly viscous greenish castor oil resinic ester alkoxylate which on average contains 17 propylene oxide units and 25.4 ethylene oxide units per molecule. The hydroxyl number of the alkoxylate is between 30 and 35.

b) Castor oil rosin ester alkoxylate di(maleic monoester)

300 p. of castor oil rosin ester alkoxylate according to Preparation Example 8a) are esterified in accordance with the hydroxyl number 32.5 with 17 parts of maleic anhydride at 75° to 80° C. over a period of 3 to 4 hours analogously to Preparation Example 2b). A light green monoester product having an acid number of 35 is obtained.

c) Triethylenetetramine salt of castor oil rosin ester alkoxylate di(maleic monoester)

300 p. of di(maleic monoester) according to Preparation Example 8b) are reacted with 27.5 parts of triethylenetetramine over a period of I to 1.5 hours. The amine salt obtained has a pH of between 8.9 and 9.3 and an amine number of about 125.3.

Preparation Example 9 a) Castor oil ethoxylate 466 p. of commercially available castor oil are heated, after addition of 10 p. of sodium methoxide (30% in methanol) in a pressure vessel to 80° C. to 90° C. with stirring, and the methanol is distilled off under reduced pressure. After increasing the temperature to 150° to 170° C., 396 parts of ethylene oxide are injected at a pressure of 4 to 6 bar. Stirring at 150° to 160° C. is then continued for one hour. The viscous green castor oil ethoxylate obtained contains on average 18 ethyleneoxy units per molecule and has a hydroxyl number of 97.6.

b) Tri(castor oil) ethoxylate succinate 200 p. of castor oil ethoxylate according to Preparation Example 9a) are heated together with 11.6 p. of succinic anhydride, which corresponds to ⅓ of the hydroxyl number, to 100° to 110° C. under nitrogen and thoroughly mixed. After addition of 0.1 p. of sodium hydroxide, the mixture is stirred at the same temperature for 4 hours. In accordance with the acid number obtained, a further 206 p. of castor oil ethoxylate according to Example 9a) are added. After addition of 2 p. of p-toluenesulfonic acid and 150 parts by volume of xylene, esterification is carried out at 155° to 165° C. for 8 hours, during which the water of reaction is removed by azeotropic distillation in a water separator. The acid number is 14.9. A further 211.6 p. of castor oil ethoxylate succinic monoester are then added, and esterification is continued for another 8 hours by removing the water of reaction at 155° to 165° C. The xylene is then distilled off, and the acid number is determined. The product has an acid number of less than 10 and a hydroxyl number of 50 to 60. In the product obtained, 3 castor oil ethoxylate units are linked by 2 succinic acid units.

c) Tri(castor oil ethoxylate) succinic ester ethoxylate 400 p. of castor oil ethoxylate succinic ester according to Preparation Example 9b) are reacted, after addition of 18 p. of sodium methoxide (30% in methanol), with 442 p. of ethylene oxide as described in Preparation Example 1a). The castor oil ester ethoxylate obtained contains 192.8 ethylene oxide units per molecule at a hydroxyl number of 22 to 28.

Preparation Example 10 a) Di(castor oil) phthalic ester 466 p. of commercially available castor oil are esterified, after addition of 37 p. of phthalic anhydride, 2 p. of p-toluenesulfonic acid and 150 ml of xylene, at 110° C. over a period of 4 hours and at 155° to 165° C. for 8 hours, and the water of reaction is removed by azeotropic distillation. After the xylene has been distilled off, a product having an acid number of 12.3 is obtained. In the product, 2 castor oil units are linked by 1 phthalic acid unit.

b) Di(castor oil) phthalic ester ethoxylate 200 p. of di(castor oil) phthalic ester according to Preparation Example 10a) are reacted, after addition of 5 p. of sodium methoxide (30% in methanol), with 176.5 p. of ethylene oxide as described in Preparation Example 1b). The castor oil ester obtained ethoxylate contains 40 ethylene oxide units per molecule and has a hydroxyl number of 55 to 65.

Preparation Example 11

Castor oil ethoxylate-succinate ethoxylate-rosin ester-sulfosuccinate 300 p. of castor oil ethoxylate-succinate ethoxylate according to Preparation Example 9c) are stirred together with 25.2 p. of disproportionated rosin, which corresponds to 2/5 of the hydroxyl number, for one hour under nitrogen. After addition of 6 p. of tin powder, 1 p. of p-toluenesulfonic acid and 150 parts by volume of xylene, esterification is carried out for 10 hours while removing the water of reaction by azeotropic distillation. After the xylene has been distilled off, the acid number is less than 20.8.2 p. of maleic anhydride, which corresponds to 3/5 of the hydroxyl number, are then introduced. Monoesterification at 75° to 80° C. is carried out for 3 hours, and the resulting product is converted to the sulfosuccinate by addition of a solution of 10.6 p. of sodium sulfite in 639 p. of water. The amount of the water added is preferably between 50 and 85% of the finished product solution. The product obtained is a sulfosuccinic monoester having a residual hydroxyl number of 3.3 in which all 5 polyoxyethylene chains have been reacted at the end group.

Preparation Example 12 a) Di(castor oil) dimeric fatty acid ester 400 p. of commercially available castor oil are esterified, after addition of 2 p. of p-toluenesulfonic acid and 150 parts by volume of xylene, with 121 p. of commercially available dimeric fatty acid (®PRIPOL) at 155° to 165° C. over a period of 8 hours, during which the water of reaction is removed by azeotropic distillation in a water separator. The xylene is then distilled off, and an acid number of 6.0 is reached. The product obtained contains 2 castor oil units linked by one dimeric fatty acid unit.

b) Di(castor oil) dimeric fatty acid ester ethoxylate 300 p. of di(castor oil) dimeric fatty acid ester according to Preparation Example 1a) are reacted, after addition of 2.5 p. of powdered sodium hydroxide, with 529 p. of ethylene oxide analogously to Preparation Example 1a). The product obtained contains on average 60 ethylene oxide units per molecule at a hydroxyl number of 50 to 60.

Preparation Example 13 a) Di(castor oil) dimeric fatty acid ester ethoxylate tetra(sulfo succinate)

300 p. of di(castor oil) dimeric fatty acid ester ethoxylate according to Preparation Example 12b) are mixed in accordance with its hydroxyl number with 28.8 p. of maleic anhydride, and the mixture is stirred at −70° to 80° C. under nitrogen for 3 hours. A solution of 37.0 p. of sodium sulfite in 679.3 parts by volume of water is run in to the maleic monoester obtained, and the batch is stirred at 70° to 80° C. for 2 to 3 hours until it has become water-soluble with the formation of a clear solution. The amount of water added with the sodium sulfite solution can be 50 to 85% by weight of the product-containing solution. The main product obtained is a sulfosuccinic monoester having a residual hydroxyl number of 8.1 in which all 4 polyoxyethylene chains have been reacted at the end group.

Preparation Example 14 a) Ricinoleic acid rosin glycerol mixed ester 298 p. of commercially available ricinoleic acid are heated together with 302 p. of disproportionated rosin to 70° to 80° C., and the mixture is stirred for one hour under nitrogen gas. After addition of 12 parts of tin powder, 4.0 parts of p-toluenesulfonic acid and 150 parts by volume of xylene, the mixture is heated at 150° to 160° C. for 16 hours, and the water of reaction is removed by azeotropic distillation. An acid number of less than 25 is obtained. 92 p. of glycerol are then added, and esterification is continued at 155° to 160° C. for another 8 hours while removing the water of reaction down to an acid number of less than 18, and the xylene is then distilled off.

b) Ricinoleic acid mixed ester alkoxylate 300 p. of ricinoleic acid mixed ester according to Preparation Example 14a) are introduced as the initial charge and reacted at 120° to 140° C. and a pressure of 3 to 4 bar with 268 parts of propylene oxide. After 1 hour of stirring, 6 parts of sodium methoxide (30% in methanol) are added, the methanol is removed, and 305 parts of ethylene oxide are introduced at the same temperature and at the same pressure conditions, and the batch is stirred at 140° to 145° C. at a pressure of 3 to 4 bar for another hour. This gives a viscous greenish ricinoleic ester alkoxylate which on average contains 10 propylene oxide units and 16 ethylene oxide units per molecule. The hydroxyl number of the alkoxylate is between 110 and 120.

Preparation Example 15 a) Ricinoleic acid mixed ester alkoxylate di(maleic monoester)

300 p. of ricinoleic acid mixed ester alkoxylate according to Preparation Example 14b) are monoesterified at 75° to 80° C. with 60.3 p. of maleic anhydride, which corresponds to a hydroxyl number of 115, over a period of 3 to 4 hours. A yellow-green monoester product having an acid number of 95 is obtained.

b) Diethylenetriamine salt 300 p. of the di(maleic monoester) according to Preparation Example 15a) are reacted at 60° to 70° C. in accordance with the acid number with 52.8 p. of diethylenetriamine over a period of 1 to 2 hours. A yellow-green, wax-like product having an amine number of between 117 and 122 is obtained.

Preparation Example 16 a) Ricinoleic acid mixed ester ethoxylate 300 p. of ricinoleic acid mixed ester according to Preparation Example 14a) are heated, after addition of 3 p. of sodium methoxide (30% in methanol), in a pressure vessel to 80° to 90° C. with stirring, and the methanol is distilled off under reduced pressure. After increasing the temperature to 150° to 170° C., 360 parts of ethylene oxide are injected at a pressure of 4 to 6 bar. Stirring at 150° to 160° C. is then continued for one hour. The wax-like green ricinoleic acid ethoxylate obtained contains on average 28 ethyleneoxy units per molecule and has a hydroxyl number of 180 to 190.

b) Castor oil mixed ester ethoxylate di(sulfosuccinate)

200 p. of castor oil mixed ester ethoxylate according to Preparation Example 14b) are esterified at 70° to 80° C. in accordance with the hydroxyl number with 64.7 p. of maleic anhydride in the presence of 0.1 p. of powdered sodium hydroxide over a period of 4 hours, and the resulting product is then converted to the sulfosuccinate by addition of a solution of 83.2 parts of sodium sulfite in 668 parts of water. The amount of the water added can be between 50 and 85% by weight of the product-containing solution. The main product obtained is a sulfosuccinic monoester having a residual hydroxyl number of 24.3 in which both polyoxyethylene chains have been reacted at the end group.

Preparation Example 17 a) Diricinoleic phthalic ester 298 p. of commercially available ricinoleic acid are esterified at 100° to 110° C. with 74 p. of phthalic anhydride in the presence of 0.4 p. of powdered sodium hydroxide over a period of 10 hours analogously to Preparation Example 10a) until an acid number of 16 is reached. After addition of 149 p. of triethanolamine, esterification is continued at 155° to 160° C. for another 8 hours with simultaneous removal of the water of reaction by azeotropic distillation. After the xylene has been distilled off, a product is obtained which has an acid number of less than 18.

b) Diricinoleic phthalic mixed ester ethoxylate 300 p. of diricinoleic phthalic mixed ester according to Preparation Example 17a) are heated, after addition of 4.5 p. of sodium methoxide (30% in methanol), in a pressure vessel to 80° to 90° C. with stirring, and the methanol is distilled off under reduced pressure. After increasing the temperature to 150° to 170° C., 860 parts of ethylene oxide are injected at a pressure of 4 to 6 bar. Stirring at 150° to 160° C. is then continued for one hour. The highly viscous green-brown ethoxylate obtained contains on average 58 ethyleneoxyunits per molecule and has a hydroxyl number of 60 to 70.

Preparation Example 18

Diricinoleic phthalic mixed ester ethoxylate di(sulfosuccinate)

300 p. of diricinoleic mixed ester ethoxylate according to Preparation Example 17b) are monoesterified at 70° to 80° C. in accordance with the hydroxyl number with 34.1 p. of maleic anhydride over a period of 3 hours, and the resulting product is reacted at the same temperature with 43.4 p. of sodium sulfite dissolved in 700 p. of water for 2 to 3 hours until it is dissolved. The main product obtained is a sulfosuccinic monoester having a residual hydroxyl number of 7.0 in which all 4 polyoxyethylene chains have been reacted at the end group.

Preparation Example 19 a) Diricinoleic succinic diglyerol ester 298 p. of commercially available ricinoleic acid are mixed at 70° to 80° C. with 50 p. of succinic anhydride under a nitrogen gas. After addition of 1.5 p. of p-toluenesulfonic acid and 200 parts by volume of xylene, esterification is carried out at 100° to 110° C. for 3 hours and then at 155° to 165° C. for 10 hours, during which the water of reaction is removed by azeotropic distillation. When the acid number is less than 20, 92 p. of glycerol are added, and esterification is continued at 155° to 165° C. for another 8 hours while again removing the water of reaction. After the xylene has been distilled off, the product has an acid number of 5.

b) Diricinoleic succinic diglyercol ester ethoxylate 200 p. of the ricinoleic mixed ester according to Preparation Example 19a) are reacted, after addition of 6 p. of sodium methoxide (30% in methanol), with 573 p. of ethylene oxide analogously to Preparation Example 1b). The product obtained contains, as the main component a di(ricinoleic acid) succinate diglycerol ester ethoxylate having on average 55 ethylene oxide units per molecule and a hydroxyl number of 65 to 75.

Preparation Example 20 a) Diricinoleic succinicdiglyercol ester ethoxylate tetra(phthalic monoester)

300 p. of the ricinoleic mixed ester ethoxylate according to Preparation Example 19b) are mixed at 70° to 80° C. in accordance with the hydroxyl number with 55.4 p. of phthalic anhydride while passing nitrogen gas over the mixture, and, after addition of 0.2 part of powdered sodium hydroxide, esterification is carried out at 100° to 110° C. for 4 hours. This gives on average one tetra(phthalic monoester) per molecule having an acid number of 59.

b) Tetradiethylenetriamine salt 300 p. of the phthalic monoester according to Preparation Example 20a) are reacted at 70° to 80° C. in accordance with the acid number with 31.5 p. of diethylenetriamine. The amine product obtained has a pH of between 8.5 and 9.5 and an amine number of about 136.

Preparation Example 21

Diricinoleic succinic diglyercol ester ethoxylate tetra(sulfo-succinate)

300 p. of the ricinoleic mixed ester ethoxylate according to Preparation Example 19b) are monoesterified at 70° to 80° C. in accordance with the hydroxyl number with 37 p. of maleic anhydride under nitrogen gas over a period of 3.5 hours, and the resulting product is then reacted at the same temperature with a solution of 47.6 p. of sodium sulfite and 714 p. of water for 2 to 3 hours until the batch has clarified. The amount of the water added can be between 50 and 85% of the product-containing solution. The main product obtained is a sulfosuccinic monoester having a residual hydroxyl number of 7.6 in which all 4 polyoxyethylene chains have been reacted at the end group.

Preparation Example 22 a) Castor oil di(2-hydroxy-3-naphthoic acid) acrylate 188 p. of 2-hydroxy-3-naphthoic acid and 466 p. of commercially available castor oil are stirred at 150° to 160° C. under reflux in the presence of 33 p. of a strongly acidic ion exchanger under a nitrogen atmosphere for 48 hours. The ion exchanger is then separated off by filtration. The acid number is 148.8.

b) Castor oil di(2-hydroxy-3-naphthoic acid) ethoxylate 300 p. of castor oil di(2-hydroxy-3-naphthoic acid) acrylate according to Preparation Example 22a) are ethoxylated, after addition of 1.5 p. of sodium hydroxide, at 170° to 180° C. and a pressure of 4 bar over a period of 2 hours with the addition of 858 p. of ethylene oxide. The light-green, slightly viscous ethoxylate obtained contains 85 mol of ethylene oxide and is soluble in water giving a clear solution. It has a hydroxyl number of 77.8.

Preparation Example 23 a) Castor oil di(2-hydroxy-3-naphthoic acid) ethoxylate 300 p. of castor oil di(2-hydroxy-3-naphthoic acid) arylate according to Preparation Example 22a) are ethoxylated, after addition of 2 p. of sodium hydroxide, at 160° to 170° C. and a pressure of 4 to 5 bar over a period of 4 hours with the addition of 1100 p. of ethylene oxide. The greenish-coloured viscous ethoxylate obtained contains on average 109 ethylene oxide units per molecule and is soluble in water giving a clear solution. It has a hydroxyl number of about 66.2.

b) Castor oil di(2-hydroxy-3-naphthoic acid) ethoxylate benzoate tetra(sulfosuccinate)

300 p. of castor oil di(2-hydroxy-3-naphthoic acid) ethoxylate according to Preparation Example 23a) are esterified, after addition of 2 p. of p-toluenesulfonic acid and 1 p. of boric acid in 200 parts by volume of xylene as the entrainer, at 160° to 165° C. with 18.5 p. of benzoic acid, which corresponds to 3/7 of the hydroxyl number, for 12 hours with constant removal of the water of reaction by azeotropic distillation. After the xylene has been distilled off, an acid number of 18 is obtained. After cooling the batch to 50° to 60° C., 19.8 p. of maleic anhydride, which corresponds to the residual hydroxyl number, are introduced, and the mixture is stirred at 70° to 80° C. under a nitrogen atmosphere for 4 hours. A solution of 25.5 p. of sodium sulfite and 698 p. of water are then added dropwise over a period of 15 to 120 minutes, and the batch is stirred until it becomes clear. Stirring at the same temperature is then continued for 1 hour. The amount of the water added can be between 50 and 85% by weight of the product-containing solution. The main product obtained is a sulfosuccinic monoester having a residual hydroxyl number of 7.2 in which all 7 polyoxyethylene chains have been reacted at the end group.

Preparation Example 24 a) Tri(castor oil) maleic ester ethoxylate 300 p. of tri(castor oil) maleic ester according to Preparation Example 5a) are heated, after addition of 9 parts of sodium methoxide (30% in methanol), in a pressure vessel to 80° to 90° C. with stirring. The methanol is distilled off under reduced pressure. After increasing the temperature to 150° to 170° C., 860 p. of ethylene oxide are injected at a pressure of 4 to 6 bar. Stirring at 150° to 160° C. is then continued for an hour. The wax-like green-brown ethoxylate obtained contains on average 19.5 ethyleneoxy units per molecule and has a hydroxyl number of 24.5.

b) Tri(castor oil) penta(maleic monoester) 1,3-propanediamine salt 400 p. of tri(castor oil) ethoxylate according to Preparation Example 24a) are monoesterified, after addition of 0.2 p. of powdered sodium hydroxide, at 70° to 80° C. in accordance with its hydroxyl number with 17 p. of maleic anhydride for 4 hours. After cooling to 50° to 55° C., 12.3 p. of 1,3-propanediamine dissolved in 430 p. of water, which corresponds to an acid number of 23.3, are added dropwise over a period of 30 to 60 minutes, and the mixture is then stirred for 2 hours. The amine salt present has a pH of 8.1 to 8.5 and an amine number of about 40 to 50.

Preparation Example 25

Tri(castor oil) penta(maleic monoester) 1,3-propanediamine ethoxylate salt 300 p. of tri(castor oil) maleic ester ethoxylate according to Preparation Example 5b) are monoesterified at 70° to 80° C. in accordance with the hydroxyl number present with 22.9 p. of maleic anhydride over a period of 4 hours with addition of 0.1 p. of powdered sodium hydroxide. After cooling to 50° to 60° C., 375 p.—which corresponds to an acid number of 44.1—of 1,3-propanediamine which is ethoxylated with 32 ethylene oxide units are added dropwise over a period of 60 to 120 minutes, and the mixture is then stirred at 20° to 25° C. for 2 hours. The amine salt adduct present has a pH of 7.5 to 8 and an amine number of about 60 to 70.

Preparation Example 26

Di(castor oil) tetra(sulfosuccinic monoester) 1,3propanediamine ethoxylate salt 300 p. of the di(castor oil) maleic ester ethoxylate according to Preparation Example 7b) are monoesterified, after addition of 0.1 p. of powdered sodium hydroxide, at 70° to 80° C. in accordance with the hydroxyl number with 11.7 p. of maleic anhydride over a period of 3 hours. After a solution of 15 parts of sodium bisulfite and 608.0 parts of water has been run in, stirring at 70° to 80° C. is continued for another 2 hours. After the temperature has dropped to 20° to 25° C., 226 parts—which corresponds to an acid number of 26.3—of 1,3-propanediamine which is ethoxylated with 32 mol of ethylene oxide are added dropwise over a period of 30 to 60 minutes, and the mixture is stirred at 20° to 25° C. for 2 hours. The amine salt present has a pH of 7.3 to 8.0 and an amine number of about 45.

Preparation Example 27 a) Castor oil 2-hydroxy-6-naphthoate 325 p. of natural castor oil are heated together with 125 p. of 2-hydroxy-6-naphthoic acid to 70° to 80° C. and stirred under nitrogen for one hour. After addition of 2 p. of p-toluenesulfonic acid and 150 parts by volume of xylene, the mixture is heated at 155° to 165° C. for 12 hours, during which 11.8 p. of water of reaction are removed in a water separator by azeotropic distillation. The xylene is then distilled off, and the acid number is determined by DIN (German Standard Specification) 53402, taking into account the naphtholic hydroxyl group. The product mixture has an acid number of about 101, according to which 68 to 70% are present as esterification product.

b) Castor oil 2-hydroxy-6-naphthoate ethoxylate 300 p. of castor oil 2-hydroxy-6-naphthoate according to Preparation Example 27a) are heated, after addition of 9 p. of sodium methoxide (30% in methanol), in a pressure vessel to 80° to 90° C. with stirring. The methanol is distilled off under reduced pressure. After increasing the temperature to 140° to 160° C., 360 p. of ethylene oxide are introduced at a pressure of 4 to 6 bar. Stirring at the same temperature is then continued for an hour. The viscous greenish castor oil ester ethoxylate obtained contains on average 85.2 ethylene oxide units per molecule and has a hydroxyl number of 33 to 35.

Preparation Example 28

Castor oil 2-hydroxy-6-naphthoate ethoxylate tri(sulfosuccinic monoester)

300 p. of the ethoxylate according to Preparation Example 27b) are monoesterified, after addition of 0.1 p. of powdered sodium hydroxide, at 75° to 80° C. in accordance with the hydroxyl number with 17.3 p. of maleic anhydride for 4 hours. After a solution of 22 p. of sodium sulfite and 630 p. of water has been run in, stirring at the same temperature is continued for 2 hours until the batch is water-soluble with the formation of a clear solution. The pH is then brought to 7 with aqueous sodium hydroxide solution. The amount of the water added can be 50 to 85% by weight of the product solution. The main product obtained is a sulfosuccinic monoester having a residual hydroxyl number of 4.3 in which all 3 polyoxyethylene chains have been reacted at the end group.

Preparation Example 29

Castor oil resin ester ethoxylate di(sulfuric monoester)

300 p. of the castor oil resin ester ethoxylate according to Preparation Example 1b) are mixed in accordance with the hydroxyl number with 14.5 p. of sulfamic acid and 3.8 p. of urea, and the mixture is stirred at 122° to 125° C. under a nitrogen atmosphere for 4 hours, during which the highly viscous reaction product (ammonium salt of the di(sulfuric monoester) of the rosin castor oil ester ethoxylated with 80 ethylene oxide units) becomes water-soluble. In order to convert it into the sodium salt, 860 p. of water and 40 ml of 1-normal sodium hydroxide solution are added to 300 p. of the ammonium salt, and the mixture is heated at 70° C. while introducing nitrogen and stirring until the ammonia has been driven off. The amount of the water added can be 50 to 85% by weight of the product-containing solution. The main product obtained is a sulfuric monoester having a residual hydroxyl number of 5.5 in which both polyoxyethylene chains have been reacted at the end group.

Preparation Example 30

Castor oil ethoxylate penta(sulfuric monoester)

300 p. of castor oil ethoxylate according to Preparation Example 9a) are diluted with 250 ml of methylene chloride and—in accordance with the hydroxyl number—34.3 p. of chlorosulfonic acid are added dropwise at 15° to 20° C., during which a gentle stream of dry nitrogen is passed through the solution, removing the escaping hydrogen chloride gas via a reflux condenser. Towards the end of the reaction the batch is warmed to 30° C. and stirred until no more hydrogen chloride gas escapes. After the methylene chloride has been distilled off under reduced pressure at 30° C., 329 g of an oil having a tritatable chlorine content of 0.04% remain as residue. For neutralization, 900 p. of water are added, and neutralization is carried out with 36.4 p. of 33% sodium hydroxide solution to a pH of 7.0. The amount of the water added can be between 50 and 85% by weight of the product-containing solution. The main product obtained is a sulfuric monoester having a residual hydroxyl number of 8.1 in which all 5 polyoxyethylene chains have been reacted at the end group.

Preparation Example 31

Castor oil di(2-hydroxy-3-naphthoic acid) ethoxylate hepta(sulfuric monoester)

300 p. of castor oil di(2-hydroxy-3-naphthoic acid) ethoxylate according to Preparation Example 23a) are diluted with 250 ml of methylene chloride, and in accordance with the hydroxyl number 41.1 p. of chlorosulfonic acid are added as described in Preparation Example 30. After the methylene chloride has been distilled off under reduced pressure at a temperature of 28° to 31° C., 331 p. of an oil having a titratable chlorine content of 0.06% are obtained. For neutralization, 900 p. of water are added, and neutralization is carried out with 51 p. of 33% sodium hydroxide solution up to a pH of 6.8 to 7.0. The amount of the water added can be between 50 to 85% by weight of the product-containing solution. The main product obtained is a sulfuric monoester mixture having a residual hydroxyl number of 9.0 in which 6 to 7 polyoxyethylene chains have been reacted at the end group.

Preparation Example 32 a) Ricinoleic acid 2-hydroxy-3-naphthoic acid arylate 188 p. of 2-hydroxy-3-naphthoic acid and 298 p. of commercially available ricinoleic acid are stirred at 110° to 120° C. in the presence of 37.5 parts of a strongly acidic ion exchanger under a nitrogen atmosphere for 36 hours and then stirred under reflux while increasing the temperature to 150° to 160° C. The acid number is about 250.

b) Ricinoleic acid 2-hydroxy-3-naphthoic acid ethoxylate 300 p. of ricinoleic acid 2-hydroxy-3-naphthoic acid arylate according to Preparation Example 32a) are ethoxylated, after addition of 1.5 p. of sodium hydroxide, at 170° to 180° C. and a pressure of 4 bar over a period of 2 hours with the addition of 860 p. of ethylene oxide. The light-green, slightly viscous ethoxylate obtained contains 32 mol of ethylene oxide and is soluble in water with the formation of a clear solution. It has a hydroxyl number o f about 89.6.

c) Ricinoleic acid 2-hydroxy-6-naphthoic acid ethoxylate tri(sulfosuccinic monoester)

300 p. of the ethoxylate according to Preparation Example 32b) are monoesterified at 75° to 85° C., after addition of 0.1 p. of powdered sodium hydroxide, in accordance with the hydroxyl number with 47.0 p. of maleic anhydride for 4 hours. After a solution of 60.4 p. of sodium sulfite and 611 p. of water has been run in, the batch is stirred at the same temperature for another 2 hours until it is water-soluble and has formed a clear solution. The pH is then brought to 7 with aqueous sodium hydroxide solution. The amount of the water added can be 50 to 85% by weight of the product solution. The main product obtained is a sulfosuccinic monoester having a residual hydroxyl number of 13.4 in which all 3 polyoxyethylene chains have been reacted at the end group.

Preparation Example 33 a) Castor oil 2-hydroxy-3-naphthanilide 257 p. of 2-hydroxy-3-naphthanilide and 466 p. of commercially available castor oil are stirred at 150° to 160° C. under reflux in the presence of 44 p. of a strongly acidic ion exchanger under a nitrogen atmosphere for 48 hours. The ion exchanger is then separated off by filtration. According to GC analysis, the arylate still contains 8.1% of unreacted 2-hydroxy-3-naphthanilide.

b) Castor oil 2-hydroxy-3-naphthanilide ethoxylate 300 p. of castor oil 2-hydroxy-3-naphthanilide according to Preparation Example 33a) are ethoxylated, after addition of 1.5 p. of sodium hydroxide, at 170° to 180° C. and a pressure of 4 bar with the addition of 865 p. of ethylene oxide over a period of 2 hours. The light-green, slightly viscous ethoxylate obtained contains 78 ethylene oxide units per molecule and is soluble in water giving clear solution. It has a hydroxyl number of 70.8.

Preparation Example 34 a) Castor oil 2-hydroxy-3-naphthanilide ethoxylate tri(sulfosuccinic monoester)

300 p. of the ethoxylate according to Preparation Example 33b) are monoesterified, after addition of 0.1 p. of powdered sodium hydroxide, at 75° to 85° C. in accordance with the hydroxyl number with 37.1 p. of maleic anhydride for 4 hours. After a solution of 47.7 p. of sodium sulfite and 630 p. of water has been run in, the batch is stirred at the same temperature for another 2 hours until it is water-soluble with the formation of a clear solution. The pH is then brought to 7 with aqueous sodium hydroxide solution. The amount of the water added can be 50 to 85% by weight of the product solution. The main product obtained is a sulfosuccinic monoester having a residual hydroxyl number of 10.5 in which all 3 polyoxyethylene chains have been reacted at the end group.

Preparation Example 35

Di(castor oil) maleic ester ethoxylate tetraoleate 300 p. of castor oil ethoxylate according to Preparation Example 7b) are stirred at 70° to 80° C. in accordance with the hydroxyl number with 33.6 p. of commercially available oleic acid under nitrogen gas for one hour. After addition of 2 p. of p-toluenesulfonic acid and 150 parts by volume of xylene, the mixture is heated at 153 to 165° C. for 18 hours, and the water of reaction is removed by azeotropic distillation. After the xylene has been distilled off, a product is obtained which has an acid number of less than 20 and in which all 4 polyoxyethylene chains have been reacted at the end group.

Comparative Example 1

11 p. of dinitroaniline are diazotized in the usual manner in a mixture of sulfuric acid and hydrochloric acid with 10.4 parts of 40% aqueous sodium nitrite solution.

Pure β-naphthol is precipitated from a solution of 8.64 parts of β-naphthol in a mixture of 100 parts of water and 8 parts of 33% sodium hydroxide solution by adding the solution dropwise to a mixture of 300 parts of water and 10 parts of 31% hydrochloric acid.

The coupling to give C.I. Pigment Orange 5 (C.I. No. 12075) is then carried out in the usual manner by running the clarified diazonium salt solution in to the suspension of the precipitated β-naphthol. The pigment is then filtered, washed with water and finally dried.

Use Example 1a

The coupling reaction to give C.I. Pigment Orange 5 (C.I. No. 12075) as described in Comparative Example 1 is repeated, except that before dropwise addition of the β-naphthol solution, 1 part of the compound according to the invention from Preparation Example 23b) is first added to the mixture of 300 parts of water and 10 parts of 31% hydrochloric acid introduced as the initial charge.

The pigment thus obtained differs from the one obtained by Comparative Example 1 by exhibiting a much yellower shade and a substantially higher color strength not only in book and offset printing but also in aqueous preparations for flexographic printing or disperse dyes. The printing inks and preparations are distinguished by a lower viscosity. Moreover, the pigment thus obtained shows higher gloss and better transparency in book and offset printing.

The same results are obtained by using the compounds according to the invention from Preparation Examples 4, 6, 13 and 28.

Comparative Example 2

34.5 parts of 4-chloro-2-nitroaniline are stirred in dilute hydrochloric acid, then diazotized in the usual manner with 34.7 parts of 40% sodium nitrite solution, and the resulting diazonium salt suspension is then clarified.

43.25 parts of 2-chloroacetic acid anilide are stirred into a mixture of 800 parts of water, 4 parts of glacial acetic acid and 8.1 parts of 33% sodium hydroxide solution. The coupling to give C.I. Pigment Yellow 3 (C.I. No. 11710) is carried out at 10° to 20° C. in such a manner that the diazonium salt solution is run in to the coupling suspension below the surface. The pH during coupling is maintained at 4 to 4.5 by addition of dilute sodium hydroxide solution. The pigment is then filtered, washed with water and finally dried.

Use Example 2a

The coupling reaction to give C.I. Pigment Yellow 3 (C.I. No. 11710) as described under Comparative Example 2 is repeated, except that 4 parts of the compound according to the invention from Preparation Example 23b or 34 are added to the suspension of the 2-chloroacet-anilide. Upon incorporation in a long-oil alkyd varnish, the pigment thus obtained exhibits a substantially higher color strength, high transparency and a greener and purer shade than the C.I. Pigment Yellow 3 prepared according to Comparative Example 2.

The same results are obtained by using the compounds according to the invention from Preparation Examples 4 and 6.

Use Example 3

60.2 parts of 1-acetoacetylamino-2,4-dimethylbenzene and 6.1 parts of 1-acetoacetylamino-2,5-dimethoxy-4-chlorobenzene are dissolved in 900 parts of water and 31 parts by volume of 33% sodiumhydroxide solution and precipitated, after addition of 1.5 parts of a fatty alcohol polyglycol ether, by means of 22 parts by volume of acetic acid. After addition of 2.5 parts of the product from Preparation Example 8, the precipitated product is coupled with a solution of tetrazotized 4,4'-diamino3,3'-dichlorobiphenyl, the tetrazonium salt solution being prepared by addition of 60 parts by volume of aqueous 5-normal sodium nitrite solution to give a mixture of 38 parts of 4,4'-diamino-3,3'-dichlorobiphenyl, 183 parts by volume of 5-normal hydrochloric acid and 520 parts of water. After coupling is complete, 2.5 parts of dehydroabietylamine are added to the pigment suspension, the suspension is made alkali, the solution containing 1.8 parts of dimethyl coconut fatty amine oxide and 36 parts of a partially hydrogenated rosin is then added, and the mixture is heated at 98° C. for 30 minutes. The pH is then brought to 4 with hydrochloric acid, and the mixture is heated at 98° C. for another 30 minutes. It is then filtered, and the product is washed and dried, giving a pigment preparation which upon incorporation in a printing ink varnish for book and offset printing produces a printing ink exhibiting very good application technology properties. The printing ink is distinguished by significantly improved flow behavior compared with a printing ink produced without adding the product from Preparation Example 15.

The same results are obtained upon using the compounds according to the invention from Preparation Examples 8c), 20b), 28) or 34).

Use Example 4

1012 parts of 3,3'-dichloro- 4,4'-diaminobiphenyl are stirred with 6000 parts of water and 2500 parts by volume of 30% hydrochloric acid and then bisdiazotized at 0° to 15° C. with 1052 parts by volume of 40% sodium nitrite solution. To prepare the coupling reaction, 1466 parts of acetoacetylaminobenzene are dissolved in 10,000 parts of water and 800 parts by volume of 33% sodium hydroxide solution, 160 parts of the surfactant prepared according to Preparation Example 11 are added, and the acetoacetylaminobenzene is precipitated by addition of 700 parts by volume of 80% acetic acid. Azo coupling is effected by slowly running in the prepared solution of the bisdiazonium salt to the suspension of the precipitated coupling component, during which the pH is maintained at about 4.5 by continuous addition of 6% sodium hydroxide solution. After coupling is complete, the acetic acid suspension is heated to 50° C., and 150 parts of dodecylbenzyldimethylammonium chloride, 750 parts of tallow fatty propylenediamine and 300 parts of bis(4-aminocyclohexyl)methane are added. The batch is heated to 90° to 100° C., and this temperature is maintained for half an hour. The mixture is then made alkali with 1500 parts by volume of 33% sodium hydroxide solution and stirred at 90° to 100° C. for a few hours. The product is then filtered, washed, dried and milled, giving a C.I. Pigment Yellow 12 (C.I. No. 21090) preparation which can be readily used for the pigmenting of toluene-based gravure printing inks. The Pigment Yellow 12 pigment preparation obtained gives very good results with respect to color strength, gloss, transparency and gradation behavior. The gravure printing inks pigmented therewith are also distinguished by an advantageously low viscosity.

The same results are obtained upon using the compounds according to the invention from Preparation Examples 2, 4, 16b) or 34).

Use Example 5

68 parts of 1,2-propanediol, 24 parts of urea, 60 parts of water, 0.8 part of preservative and 28 parts of the product from Preparation Example 1 are introduced into a milling device 11 in capacity as the initial charge and homogenized.

After stirring in 200 parts of C.I. Pigment Green 7 (C.I. No. 74260) using a dissolver, 1100 parts of siliquarzite beads 1 mm in diameter are added, and the mixture is milled in a batchwise stirred ball mill for one hour. The mill base is then diluted with a further 19.2 parts of water, separated from the milling medium and deaerated, giving a stable, readily flowable pigment dispersion having a pigment content of 50%. On incorporation in various emulsion paints, the pigment preparation shows excellent flocculation stability.

The same results are obtained upon using the compounds according to the invention from Preparation Examples 3b), 7b), 22b) or 34).

Use Example 6

Analogously to Use Example 5, 188 parts of C.I. Pigment Blue 15:3 (C.I. No. 74160) are dispersed in a bead mill in a mixture of 76 parts of 1,2-propanediol, 0.8 part of preservative, 16 parts of urea, 70 parts of water and 30 parts of the product from Preparation Example 9.

Dilution with 19.2 parts of water gives a stable, readily flowable pigment dispersion having a pigment content of 47%. In addition to excellent flocculation stability upon incorporation in various emulsion paints, the preparation is highly suitable for the pigmenting of textile printing pastes.

The same results are obtained upon using the compounds according to the invention from Preparation Examples 1), 3b) and 22b).

Use Example 7

Analogously to Use Example 5, 160 parts of C.I. Pigment Red 146 (C.I. No. 12 485) are dispersed in a bead mill in a mixture of 76 parts of 1,2-propanediol, 0.8 part of preservative, 20 parts of urea, 72 parts of water and 32 parts of the product from Preparation Example 22b).

Dilution with 39.2 parts of water gives a stable, readily flowable pigment dispersion having a pigment content of 40%. Owing to its very good flocculation stability, the preparation is suitable for the pigmenting of aqueous emulsion paints, aqeous-alcoholic flexographic printing inks and textile printing inks.

The same results are obtained upon using the compounds according to the invention from Preparation Examples 5), 6), 23a) and 27b).

Use Example 8

Analogously to Use Example 5, 140 parts of C.I. Pigment Yellow 83 (C.I. No. 21108) are dispersed in a bead mill in a mixture of 60 parts of 1,2-propanediol, 0.8 part of preservative, 53 parts of water and 114 parts of a 35% aqueous solution of the product described in Preparation Example 6. Dilution with 32.2 parts of water gives a stable, readily flowable pigment dispersion having a pigment content of 35%.

The pigment dispersion obtained is highly suitable for coloring paper paste and is distinguished in this application in particular by a low tendency to foaming.

Significantly improved results are also obtained upon using the compounds according to the invention from Preparation Examples 11), 21), 23b), 27b) or 34).

Use Example 9

138 parts of C.I. Pigment Brown (C.I. No. 12480) are milled in a stirred ball mill together with 127 parts of a 35% aqueous solution according to Preparation Example 6 and 134 parts of water in the presence of siliquarzite beads (1 mm in diameter), and the resulting dispersion is then diluted by addition of 129 parts of water. The highly flowable pigment dispersion obtained in this manner is highly suitable for the dyeing and pigmenting of leather, for the standardization of gravure and flexographic printing inks and for the coloration of paper paste.

Use Example 10

99 parts of C.I. Sulfur Brown 16 (C.I. No. 53 285) are milled in a stirred ball mill together with 229 parts of a 35% aqueous solution according to Preparation Example 6, and the resulting dispersion is then diluted by addition of 58 parts of water. The pigment dispersion obtained is suitable in particular for the dyeing of leather by the exhaust method and equally for surface dyeing.

Use Example 11

50 parts of C.I. Disperse Orange 13 (C.I. No. 26 080) are milled in a stirred mill together with 85.7 parts of a 35% aqueous solution according to Preparation Example 6 and 110 parts of water for 4 hours until a fine dispersion is obtained. After addition of 50 parts of water, a 20% dye paste is obtained which has a very good shelf life and very good flow behavior and is suitable for the dyeing polyester, polyester/wool and polyester/viscose yarns.

Use Example 12

75 parts of C.I. Pigment Black 7 (C.I. No. 77266) are milled together with 49 parts of a 50% aqueous solution according to Preparation Example 8 and 80 parts of water analogously to Use Example 4, and the resulting dispersion is diluted with a further 13 parts of water. The carbon black dispersion obtained has good flow behavior and is highly suitable for the dyeing and pigmenting of leather by the bath and dipping methods.

Use Example 13

137 parts of zirconium carbonate are milled in a stirred ball mill together with 127 parts of a 35% aqueous solution according to Preparation Example 6 and 100 parts of water in the presence of siliquarzite beads (1 mm in diameter), and a further 37 parts of water are added. The zirconium carbonate dispersion has a long shelf life and is suitable in particular for the tanning of leather.

Use Example 14

50 parts of titanium dioxide are milled together with 46 parts of a 35% aqueous solution according to Preparation Example 26 and 48.5 parts of water analogously to Use Example 12 to give a fine dispersion. The titanium dioxide suspension obtained is very stable and highly suitable for the dyeing of leather by customary methods.

Use Example 15

75 parts of methylnaphthalene are stirred together with 25 parts of the diethylenetriamine salt according to Preparation Example 6 until a homogeneous mixture is obtained. The concentrate is then made up to 1000 parts by volume with water. This gives a finely disperse carrier emulsion which when used in the customary dilution (1:10) has excellent stability and can be used over an extended period of time.

Use Example 16

70 parts of an aromatics-containing mineral oil are stirred together with 20 parts of the diethylenetriamine salt according to Preparation Example 15 and 10 parts of the ethoxylate according to Preparation Example 12 until a homogeneous mixture is obtained, which is then diluted with water to 900 parts by volume. This gives a finely disperse to transparent mineral oil emulsion which, after being diluted 1:9, exhibits, apart from excellent stability over an extended period of time, also anticorrosive properties in accordance with DIN 51 360.

Use Example 17

50 parts of the crop protection agent 2-carbomethoxyaminobenzimidazole are milled in a 1 liter stirred mill together with 68 parts of a 35% aqueous solution according to Preparation Example 6 and 82 parts of water until a fine dispersion is obtained. After the grinding medium has been separated off, a very stable dispersion having good suspending power without forming sediments is obtained. The same results are obtained upon using the compounds according to the invention from Preparation Examples 13), 16b) and 23b).

What is claimed is:

1. A compound based on a castor oil or a ricinoleic acid, composed of
a) 1 to 10 divalent to nonavalent units of the formula (Ia)

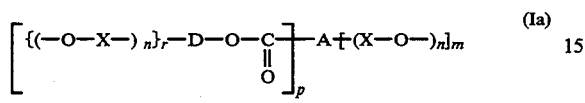

b) 1 to 72 monovalent radicals of the formula (Ib)

and in the case where two or more units of the formula (Ia) are present, additionally of
c) 1 to 9 divalent groups of the formula (Ic),

each of the free valences shown in formula units (Ia) being defined such that each, independently of the others, is directly linked to a formula unit (Ib) or a valence of the formula unit (Ic), and, in formula units (Ia) to (Ic)

A being a radical selected from the group consisting of a natural castor oil, a modified castor oil, a natural ricinoleic acid and a modified ricinoleic acid;

D being a direct bond or a divalent radical selected from the groups consisting of a straight-chain dihydric alcohol, a branched dihydric alcohol, a straight-chain or branched trihydric alcohol, a straight-chain or branched tetrahydric alcohol, a straight-chain or branched pentahydric alcohol, a straight-chain hexahydric alcohol, a branched hexahydric alcohol said dihydric and hexahydric alcohols having 2 to 8 carbon atoms, and said tri-, tetra-, and pentahydric alcohols having 2 to 6 carbon atoms, and an alkylolamine

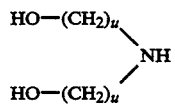

and

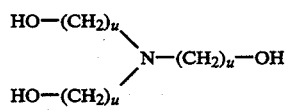

in which a is an integer from 0 to 4, u and v are identical or different and are an integer from 2 to 14 each or a portion of the OH, NH or $NH_2$ groups being alkoxylated;

E being a radical selected from the group consisting of a straight-chain aliphate, a branched aliphate, a cyclic aliphate, mid aliphates having 0 to 20 carbon atoms, an aromate having 6 to 10 carbon atoms, an alkenyl based on a dimerized unsaturated $C_{28}$–$C_{72}$-fatty acid, —CH=CH—, —$CH_2CH(SO_3M)$— and —$CH(SO_3M)CH_2$—, in which M is a cation;

X being a divalent radical selected from the group consisting of —$CH_2CH_2$—, —$CH(CH_3)CH_2$— and —$CH_2CH(CH_3)$—;

Z being identical or different radicals $Z^1$ to $Z^6$, in which $Z^1$ is hydrogen, $Z^2$ is an acyl radical of the formula $R^1$—CO—, in which $R^1$ is a radical selected from the group consisting of phenyl, naphthyl, and hydroxynaphthyl, $Z^3$ is an acyl radical selected from the group consisting of an unmodified natural resin acid and a modified natural resin acid, $Z^4$ is an acyl radical selected from the group consisting of a dicarboxylic acid and a tricarboxylic acid said acids based on a dimerized or trimerized $C_{28}$–$C_{72}$-fatty acid, a saturated $C_8$–$C_{22}$-fatty acid and a unsaturated $C_8$–$C_{22}$-fatty acid, radicals $Z^5$ are identical or different radicals of the formulae —CO—$(CH_2)_q$—COOM, —CO—CH=CH—COOM, —CO—$CH_2$—$CH(SO_3)M$)—COOM, —CO—$CH(SO_3M)$—$CH_2$—COOM and —OC—$C_6H_4$—COOM, in which q is an integer from 0 to 10, $Z^6$ is —$SO_3M$, in which M is a radical selected from the group consisting of hydrogen; an alkali metal; one equivalent of an alkaline earth metal, an oxyalkyl radical of the formula (X—O—)$_n$H; an ammonium group which is unsubstituted or substituted by one to four $C_1$–$C_5$-alkyl radicals or one to four $C_2$–$C_5$-alkylol radicals; an ammonium group obtained from ammonia or from $C_1$–$C_5$-alkylamines or $C_2$–$C_5$-alkylolamines by an addition reaction with 1 to 150 ethylene oxide or propylene oxide units or a combination of ethylene oxide and propylene oxide units; a group of the formula (II)

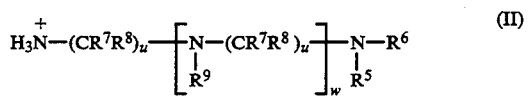

in which $R^9$, $R^5$ and $R^6$ are identical or different and are a hydrogen atom or a hydroxylalkyl group having 1 to 6 carbon atoms and $R^7$ and $R^8$ are identical or different and are hydrogen or methyl, each u is identical to or different from the others and is an integer from 2 to 14 and w is an integer from zero to 25; and a group of the formula (III)

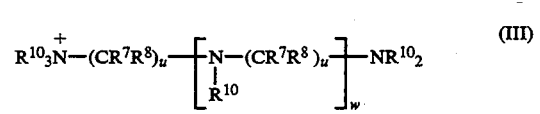

in which $R^{10}$ is the group H—(O—X—)$_y$, in which X has the abovementioned meanings and y is an integer from 1 to 100, m, in the case where A is a ricinoleic acid radical being the number 1, and, in the case where A is a castor oil radical, being a number from 1 to 3, n being a number from 1 to 250, p, in the case where A is a castor oil, being the number 0, and, in the case where A is a ricinoleic acid radical, being the number 1, and r being a number from 1 to 6,
and at least one radical Z being a radical from the group $Z^2$, $Z^3$ and $Z^5$; or at least two units of the formula (Ia) being linked to one another via a divalent group of the formula (Ic) and Z having the meanings of $Z^1$ to $Z^6$.

2. A compound as claimed in claim 1, consisting of 1 to 5 divalent to nonavalent units of the formula (IA), in which
A is the radical of a natural or modified castor oil and p is therefore the number 0,
X is —$CH_2CH_2$— and
n is an integer from 5 to 125.

3. A compound as claimed in claim 1, wherein n is an integer from 10 to 80.

4. A compound as claimed in claim 1, consisting of 1 to 5 divalent to nonavalent units of the formula (Ia), in which
A is the radical of a natural or modified ricinoleic acid, p is the number 1, and m is a number from 1 to 3,
D is a divalent radical selected from the group consisting of a straight-chain di- to hexahydric alcohol, a branched di- to hexahydric alcohol, said alcohol having 2 to 6 to carbon atoms, a $C_2$-$C_3$-alkylolamine, $C_2$-$C_3$-alkylol-$C_2$-$C_3$-alkylenediamine, $C_2$-$C_3$-alkylol-di-$C_2$-$C_3$-alkylenetriamine and $C_2$-$C_3$-alkyloltri-$C_2$-$C_3$-alkylenetetramine,
X is —$CH_2CH_2$— and
n is an integer from 5 to 125.

5. A compound as claimed in claim 1, consisting of 1 to 23 monovalent radicals of the formula (Ib), in which the radicals Z are identical or different radicals of the formulae $Z^2$, $Z^3$ and $Z^5$.

6. A compound as claimed in claim 1, consisting of 2 to 9 monovalent radicals of the formula (Ib), in which the radicals Z are identical or different radicals of the formulae $Z^3$ and $Z^5$.

7. A compound as claimed in claim 1, consisting of 1 to 4 divalent groups of the formula (Ic), in which
E is a radical selected from the group consisting of a straight-chain, branched or cyclic aliphatic alkylene radical having 1 to 10 carbon atoms; a phenylene radical; —CH=CH—, —$CH_2CH(SO_3M)$— and —$CH(SO_3M)CH_2$— in which M is a cation.

8. A compound as claimed in claim 1, consisting of 1 to 4 divalent groups of the formula (Ic), in which E is a radical selected from the group consisting of methylene, ethylene, propylene, butylene, pentylene, hexylene and decylene.

9. A compound as claimed in claim 1, wherein $Z^2$ is a radical of a carboxylic acid selected from the group consisting of benzoic acid, 1-naphthoic acid, 2-naphthoic acid and a hydroxynaphthoic acid.

10. A compound as claimed in claim 1, wherein the resin acids on which the acyl radical $Z^3$ is based are those present in commercially available rosin types.

11. A compound as claimed in claim 1, wherein $Z^3$ is a radical of an acid selected from the group consisting of oxalic acid, malonic acid, succinic acid, glutaric acid, adipic acid, pimelic acid, suberic acid, azelaic acid, sebacic acid, phthalic acid, isophthalic acid, terephthalic acid, maleic acid, fumaric acid and sulfosuccinic acid.

12. A compound as claimed in claim 1, wherein
M is a radical selected from the group consisting of a hydrogen; an alkali metal; one equivalent of an alkaine earth metal; an ammonium group which is substituted by one to four $C_1$-$C_5$-alkyl radicals or one to four $C_2$-$C_5$-alkylol radicals, an ammonium group obtained from ammonia or from $C_1$-$C_5$-alkylamines or $C_2$-$C_5$-alkylolamines by an addition reaction with 5 to 30 ethylene oxide or propylene oxide units or a combination thereof; a group of the formula (II)

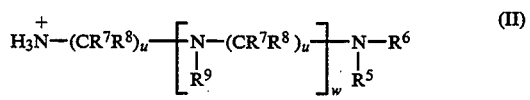

in which $R^6$, $R^5$ and $R^6$ are identical or different and are a hydrogen atom or hydroxyalkyl having 2 to 3 carbon atoms and $R^7$ and $R^8$ are identical or different and are hydrogen or methyl, each u is identical to or different from the others and is an integer from 2 to 3 and w is an integer from zero to 5; and a group of the formula (III)

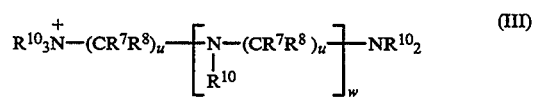

in which $R^{10}$ is the group H(—O—X—)$_y$, and y is an integer from 1 to 30.

* * * * *